United States Patent [19]

McNatty et al.

[11] Patent Number: 4,749,567
[45] Date of Patent: Jun. 7, 1988

[54] METHOD AND PRODUCT FOR INCREASING FERTILITY IN SHEEP USING MILK PROTEIN CONJUGATES

[75] Inventors: Kenneth P. McNatty; Anton F. Erasmuson, both of Upper Hutt; Douglas R. Crump, Wellington, all of New Zealand

[73] Assignee: The Director General of the Ministry of Agriculture and Fisheries, Wellington, New Zealand

[21] Appl. No.: 922,858

[22] Filed: Oct. 24, 1986

[30] Foreign Application Priority Data

Oct. 29, 1985 [NZ] New Zealand .................. 213974

[51] Int. Cl.$^4$ ................ A61K 39/385; C07K 17/016
[52] U.S. Cl. ........................................ 424/88; 424/85; 530/406; 530/410; 530/832; 260/397.5
[58] Field of Search .................. 530/410, 406, 832; 424/85, 88; 260/397.5

[56] References Cited

U.S. PATENT DOCUMENTS

| | | | |
|---|---|---|---|
| 4,150,105 | 4/1979 | Gross | 530/406 X |
| 4,197,286 | 4/1980 | Rao | 530/406 X |
| 4,331,657 | 12/1982 | Cox et al. | 424/88 |
| 4,457,914 | 7/1984 | Cox et al. | 424/88 |

OTHER PUBLICATIONS

J. Endocrinol. 81 (1979), 249–259, Martenz et al.
Aust. J. Exp. Agric. Anim. Husb. 19 (1979), 673–678, Martin et al.
Proc. Aust. Soc. Anim. Prod. 15 (1984), 191–194, Scaramuzzi.
J. Reprod. Fert. 75 (1985), 121–131, McNatty et al.

Primary Examiner—Howard E. Schain
Attorney, Agent, or Firm—Ladas & Parry

[57] ABSTRACT

A product and method for increasing fertility in sheep. By "increasing fertility" is meant increasing the potential of a flock of sheep to multiply by increasing ovulation in ewes. The product is an immunogenic conjugate of 4-androstene-3, 17-dione and a soluble milk protein (SMP): 6-hydroxyandrost-4-ene-3, 17-dione 6-hemisuccinyl: SMP. The method comprises immunizing the ewes in a flock of sheep against 4-androstene-3, 17-dione by administering 6-hydroxyandrost-4-ene-3, 17-dione 6-hemisuccinyl SMP at the rate of 3 to 5 mg per ewe. In previously untreated ewes, two administrations are required at between 8 to 9 and 4 to 5 weeks before the planned commencement of mating. Subsequent administrations are annually and are recommended at 5 weeks before the commencement of mating.

16 Claims, No Drawings

METHOD AND PRODUCT FOR INCREASING FERTILITY IN SHEEP USING MILK PROTEIN CONJUGATES

BACKGROUND OF THE INVENTION

1. Field of the Invention

This invention relates to a novel immunogenic steroid-protein conjugate and to its administration to ewes in a flock of sheep to increase the fertility of the flock. By "increasing fertility" is meant increasing the potential of a flock of sheep to multiply by increasing ovulation in ewes.

2. Description of the Prior Art

Increasing the naturally occuring rate at which a flock of sheep will reproduce has long been the object of study. The fertility or rate of multiplication of a species is affected by many factors including the genetic make-up and nutrition of an animal.

It is known that the ovulation rate in sheep may be increased by immunising sheep against certain steroid hormones. It is of great commercial importance to the farming community if the fertility of sheep may be increased effectively and inexpensively to reliably produce increased lambing percentages.

It has been discovered that the immune response system of an animal can be manipulated to affect the oestrous cycle including the ovulation rate.

The use of an immunogenic steroid-protein conjugate has been suggested where the protein is a serum albumin and the effectiveness or rate of administration is critically influenced by the level of steroid binding antibody titre in peripheral plasma before, during and after the mating period.

Such methods are difficult to plan, monitor and control particularly as the relationship between steroid antibody titre and ovulation-rate is obscure.

The object of the present invention is to provide a method of increasing fertility in sheep which is achieved by one or two administrations of an agent to a ewe in a year and which does not require blood level monitoring or sophisticated dosage effectiveness analysis.

SUMMARY OF INVENTION

Broadly, in one aspect, the invention provides a conjugate of 4-androstene-3,17-dione and a soluble milk protein (hereinafter SMP).*

*To be immunogenic the SMP needs to be derived from an animal source other than sheep. That is, the SMP must be a foreign protein to sheep.

The 4-androstene-3,17-dione may be conjugated with SMP by known methods to any position on the steroid molecule. However, the preferred position is at the 6-position. The preferred steroid protein conjugate is 6-hydroxyandrost-4-ene-3,17-dione 6-hemisuccinyl SMP.

In another aspect there is provided a method of preparing the 6-hydroxyandrost-4-ene-3,17-dione 6-hemisuccinyl SMP conjugate comprising the steps of:

(1) reaction of androst-4-ene-3,17-dione with acetic anhydride to produce 3-acetoxyandrost-3,5-diene-17-one, (2) addition of meta-chloroperbenzoic acid to the product of step (1) and reaction to form a mixture of 6α- and 6β-hydroxyandrost-4-ene-3,17-dione, (3) reacting the product of step (2) with succinic anhydride to produce 6-hydroxyandrost-4-ene-3,17-dione hemisuccinate, (4) reacting the product of step (3) with SMP so that the free acid group of 6-hydroxyandrost-4-ene-3,17-dione hemisuccinate is linked through the 6-hydroxyl group to the free amino residues in the proteins to form a conjugate 6-hydroxyandrost-4-ene-3,17-dione 6-hemisuccinyl SMP.

In a further aspect of the invention there is provided a sheep fertility increasing agent comprising an effective amount of a 6-hydroxyandrost-4-ene-3,17-dione 6-hemisuccinyl SMP.

In a further aspect of the invention there is provided a method of increasing fertility in a flock of sheep comprising the administration of a fertility increasing amount of the above agent to the ewes of the flock.

DETAILED DESCRIPTION OF THE INVENTION

The above agent is hereinafter referred to as the androstenedione-SMP vaccine.

The use of SMP rather than previously used immunogenic proteins such as bovine serum albumin has the unexpected advantage of inducing a more uniform antigenic response in a group of treated animals. Preferred SMP's are soluble whey protein concentrates having a protein content of above 50% by weight. Such whey protein concentrates are readily available as by-products of cheese or casein production. For example a suitable SMP may be derived by the ultrafiltration of rennet casein whey. A typical composition of such a whey protein concentrate would be 56% protein, 28% lactose and the balance comprising moisture, fat and ash. Preferred SMP's are chosen from the ALACEN range of whey protein concentrates marketed by the New Zealand Dairy Board. ALACENS have protein contents ranging from about 35 to about 80% but the preferred ALACEN products are those with protein contents above 50%. Commercially, the ALACENS are used widely as an egg white substitute, food binder and filler. The protein moiety is predominantly β-lactoglobulin (mw=36,000) and α-lactalbumin (mw=14,400).

Antibody titre is defined as that dilution of immune serum required to bind 50% of 30 pg of [1,2,6,7(n)-$^3$H]androst-4-ene-3,17-dione (304 mCi/mg).

The production of 6-hydroxyandrost-4-ene-3,17-dione 6-hemisuccinyl SMP involves conversion of androstenedione into a form appropriate for conjugation to SMP.

Preferably, the process comprises the following steps:

(1) reaction of androst-4-ene-3,17-dione with acetic anhydride to produce 3-acetoxyandrost-3,5-diene-17-one.

(2) reaction of the product of (1) to form 6(β) and (6α)hydroxy-androst-4-ene-3, 17-dione.

(3) reacting the product of step (2) with succinic anhydride to produce 6-hydroxyandrost-4-ene-3,17-dione hemisuccinate.

(4) reacting the product of step (4) with SMP to form a conjugate.

The progress of the process is illustrated by the following formulae:

androst-4-ene-3,17-dione

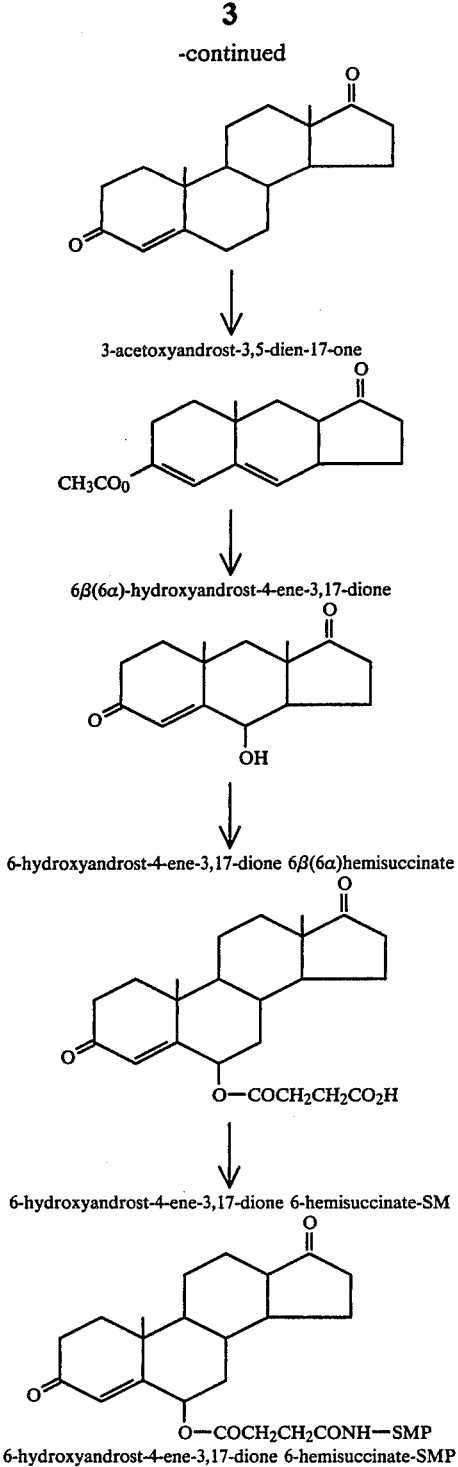

3-acetoxyandrost-3,5-dien-17-one

6β(6α)-hydroxyandrost-4-ene-3,17-dione 6-hydroxyandrost-4-ene-3,17-dione 6β(6α)hemisuccinate 6-hydroxyandrost-4-ene-3,17-dione 6-hemisuccinate-SM 6-hydroxyandrost-4-ene-3,17-dione 6-hemisuccinate-SMP In further describing the above reaction, reference is made to the following Examples:

EXAMPLE 1

The synthesis of 3-acetoxyandrosta-3,5-dien-17-one from androstenedione.

To androstenedione (10 g) in ethyl acetate (500 ml) was added a mixture of acetic anhydride (96 ml), perchloric acid (0.25 ml, 62%), and ethyl acetate (400 ml). The solution was stirred at room temperature for 5 min and was then poured into saturated aqueous sodium bicarbonate (200 ml). The organic phase was then washed with saturated sodium bicarbonate (2×200 ml) and dried with sodium sulphate. The solvents were removed under vacuum using a water pump and finally an oil pump was used to remove the excess acetic anhydride. The final traces of acetic anhydride were removed by evaporating off methanol containing a trace of pyridine leaving a white solid residue. Thin-layer chromotography (TLC; ethylacetate-hexane; 9:1) of the residue showed no starting material. Analysis of the solid by Nuclear Magnetic Resonance (NMR) spectroscopy produced the following: NMR (CDCl$_3$) δ0.94 (S, C$_{18}$), 1.07 (S, C$_{19}$), 2.13 (S, OCOCH$_2$CH$_3$), 5.45 (M, C$_6$H), 5.57 M, C$_4$H).

EXAMPLE 2

The synthesis of 6-hydroxyandrost-4-ene-3,17-dione from 3-acetoxyandrosta-3,5-dien-17-one Meta-chloroperbenzoic acid (11-25 g) was added to the crude 3-acetoxyandrosta-3,5-dien-17-one (i.e., from 15 g of androst-4-ene-3,17-dione) in dioxan (500 ml) and water (5 ml) and cooled to 5° C. in an ice bath. The reaction mixture was then kept at this temperature for 24 h and then diluted with water (500 ml) and extracted with ethyl acetate (3×500 ml). The organic phase was washed with sodium bisulphite (200 ml, 10%), after which a negative starch iodide test was obtained. The organic phase was then washed with a saturated solution of sodium bicarbonate (3×100 ml), a saturated solution of sodium chloride (1×100 ml) dried with sodium sulphate and evaporated to yield a solid (21.7 g). TLC (hexane-ethyl acetate, 1:3) showed no starting material and largely 6β and 6α forms of hydroxyandrost-4-ene-3,17-dione. NMR showed 6β and 6α-hydroxyandrost-4-ene-3,17-dione in a ratio of approximately 4:1. Crystallization of 16.4 g of the crude product from ethyl acetate-hexane (1:3) gave 7.75 g of 6α+6β-hydroxyandrost-4-ene-3,17-dione (with a similar 6α:6β ratio as for crude). The 6α and 6β isomers can be optionally separated if desired although both isomers alone or in admixture can be used. Recrystallization from ethyl acetate gave pure 6β-hydroxyandrost-4-ene-3,17-dione (2.4 g). And, a second crop of crystals contained the 6β and 6α isomers.

6β hydroxy isomer. NMRδ (CDCl$_3$) 0.95 (S, C$_{18}$), 1.41 (S, C$_{19}$), 4.45 (M, 6αH), 5.35 (bs, C$_4$H).

6α hydroxy isomer. NMRδ (CDCl$_3$) 0.94 (S, C$_{18}$), 1.25 (S, C$_{19}$), 4.35 (M, 6βH), 6.20 (bs, C$_4$H).

The 6β and 6α hydroxy compounds can be separated by column chromatography on silica gel using hexane-ethyl acetate mixtures as the eluting solvent. By this technique 10 g of crude 3-acetoxyandrosta-3,5-dien-17-one gave 3.45 g of 6β-hydroxy-androst-4-ene-3,17-dione.

EXAMPLE 3

The synthesis of 6-hydroxyandrost-4-ene-3,17-dione 6-hemisuccinate

Succinic anhydride (6.5 g) was added to 6β-hydroxyandrost-4-ene-3,17-dione (3.3 g) in dry pyridine (20 ml) and the mixture was heated at 100° C. in a nitrogen atmosphere for 24 h. The pyridine was removed in the oil-pump and the residue taken up in chloroform:water and the phases separated. The water phase was further extracted with chloroform and the combined chloroform extracts were dried and evaporated. The residue in ethyl acetate (50 ml) was then extracted into a saturated solution of sodium bicarbonate (3×30 ml) which was then neutralised with concentrated hydrochloric acid.

Thereafter the desired product was extracted back into chloroform (3×50 ml) which was then dried and evaporated to yield a solid product. The solid was tritiated with diethyl ether, filtered, washed with ethanol and then dried to yield the 6-hemisuccinate derivative (2.85 g). Crystallation of the mother liquors from ethyl acetate yielded a further 0.15 g (total 3 g, 68%).

NMR$\delta$ (CDCl$_3$) 0.95 (S, C$_{18}$Me), 1.3 (S, C$_{19}$Me), 2.65 (Bs, succinyl methylenes), 5.5 (M, 6$\alpha$H), 5.96 (S, 4H).

EXAMPLE 4

Synthesis of 6-hydroxyandrost-4-ene-3,17-dione-6 hemisuccinyl SMP.

6-Hydroxyandrostenedione (2.012 g), N-hydroxysuccinamide (0.691 g) and dicyclohexyl carbodiimide (1.4 g) were mixed with 50 ml of tetrahydrofuran for 20 h at room temperature. Citric acid (0.25 g) was then added to degrade the excess carbodiimide and stirring was continued for a further hour. The mixture was filtered to remove dicyclohexylurea, the precipitate washed with dichloromethane (20 ml) and the resulting filtrate evaporated under reduced pressure to leave a gum or resin. The resin was redissolved in about 10 ml of a dichloromethane, ethyl acetate solution (50:50 vol.), and chromatographed through a silica gel column (40 cm×2 cm) using the 50:50 dichloromethane, ethyl acetate solution. The first 50 ml eluted through the column was evaporated to leave a resin which was dried further in a dessicator. Subsequently, the resin (2 g) in 10 ml tetrahydrofuran was added to 10 g of a whey protein concentrate having approximately 76% of protein content in 250 ml water and the mixture stored for 2 h at room temperature. The yellow milky mixture was then centrifuged at 1500 g for 10 min, and the supernatant freeze-dried to produce 9.9 g of conjugate (i.e., 6-hydroxyandrost-4-ene-3,17-dione-6 hemisuccinyl SMP).

Although the androstenedione-SMP vaccine may be formulated in at least two ways (see below), the injection sequence to enhance lambing-rates in ewes is the same. The first year of treatment, two injections are required, the first being at least 8 weeks before the planned commencement date of mating. The second injection which is identical to the first should be administered 21 to 28 days after the first injection. In the second or subsequent years of treatment, only one injection is required. It is strongly recommended with respect to optimising mating efficiency that rams are kept well away from all immunised ewes until the fifth week after the second injection in the first year or the booster injection in subsequent years. Failure to observe this latter procedure results in a low mating frequency over the first one or two oestrous cycles, thereby leading to prolonged intervals of lambing.

The preferable, although not critical, site of vaccination is a subcutaneous site at the back of the neck with the repeat injection being at a separate location in the neck. The immunisation procedure is not recommended for out-of-season breeding practices. The procedure may be helpful in advancing the onset of the natural breeding season. However, at present, the abovementioned immunisation procedures are recommended solely for enhancing lambing rates during a normal breeding season.

It has been established that the vaccination procedures increase lambing rates by enhancing the number of ovulations at each oestrus after the second or booster injection. The underlying mechanisms by which the vaccination procedure enhances ovulation rates is not known, however, a possible mechanism is discussed below.

The mechanisms by which the prior art "blood titre level dependent" vaccines enhance ovulation-rates in sheep are obscure (Scaramuzzi, R. J. (1984) "Changes in pituitary-ovarian functions in ewes immune to steroid hormones". *Proc. Austr. Soc. Anim. Prod.* 15, 191-194).

In sheep breeds such as the Romney ewe, the reasons why some animals experience twin ovulations while others have one ovulation is due, at least in part, to higher blood concentrations of follicle-stimulating hormone (FSH) during the luteal phase of the oestrous cycle around the time of luteolysis (McNatty, K. P., Hudson, N., Gibb, M., Ball, K., Henderson, K. M., Heath, D. A., Lund, S. & Kieboom, L. E. (1985) "FSH influences follicle viability, oestradiol biosynthesis and ovulation-rate in Romney ewes", *J. Reprod. Fert.* 75, 121-131). This difference in plasma FSH between animals which ovulate 1 and 2 follicles is extremely small and is, on average, about 13%. That the increased FSH blood levels are directly responsible for the ovulation-rate differences was confirmed by infusing additional FSH to Romney ewes at −48 to −24 hours or −24 to 0 hours from the onset of luteolysis to raise the blood levels to 121% of those before treatment. This additional FSH significantly increased the twinning-rates in the ewes (McNatty et al., supra). However, in ewes immunized against prior art "blood titre level dependent" steroid vaccines, the consequences of the treatment are decreased levels of FSH during the luteal phase of the oestrous cycle (Scaramuzzi, supra). Also in ewes immunized against androstenedione-11$\alpha$-hemisuccinyl-bovine serum albumin (BSA), the blood levels of FSH during the luteal phase were also suppressed compared to control animals: (Martensz, N. D. & Scaramuzzi, R. J. (1979) "Plasma concentrations of luteinizing hormone, follicle-stimulating hormone and progesterone during the breeding season in ewes immunized against androstenedione or testosterone", *J. Endocrinol.* 81, 249-259). Collectively therefore, it seems unlikely that the above prior art vaccine or similar BSA-related products increase ovulation-rates by enhancing the blood levels of FSH in sheep.

In contrast to the above findings, the immunization of sheep with a 6-hydroxyandrost-4-ene-3,17-dione 6-hemisuccinyl SMP of the present invention leads to a significant elevation of the plasma FSH concentrations around the time of luteolysis. This was demonstrated as outlined below. Fourteen Romney ewes were immunized with androstenedione-SMP vaccine using DEAE dextran adjuvant. Another fourteen untreated Romney ewes were kept as controls. At 10 days after the second (booster) injection in the treated group, all animals were at the 9th or 10th day of the oestrous cycle. On this day, all animals (treated+controls) were bled hourly for 48 hours, injected with 125 $\mu$g (cloprostenol to induce luteolysis and then bled hourly for another 24 hours. At 36 to 54 hours after cloprostenol all animals displayed oestrous activity (i.e., were mated with a vasectomized ram) and 7 days later were exampled by laparoscopy to determine the number of ovulations. The mean±s.e.m. ovulation-rate in the androstenedione-alacen treated group was 1.6±0.2 whereas in the untreated group the mean±s.e.m. ovulation rate was 1.1±0.1. The ovulation-rate difference between the two groups of ewes was statistically significant at $p<0.05$. When the 24 hour mean values for FSH (see Table 1) both before and after cloprostenol were analysed by two-way analysis of variance with the two variables being treatment and time, both the effects of immunization and time of sampling were statistically significant at the 5% level. The overall treatment mean±s.e.m. for FSH was 2.5±0.2 ng/ml whereas for the controls, the overall mean was 2.2±0.2 ng/ml.

TABLE 1

FSH levels* in blood of ewes immunized with androstenedione-alacen conjugate and control ewes with respect to time of cloprostenol injection given at time 0

| | Time before and after cloprostenol injection (h) | | |
|---|---|---|---|
| | −48 to −24 | −24 to 0 | 0 to +24 |
| Treated (n = 14) | 2.7 | 2.6 | 2.1 |
| Controls (n = 14) | 2.3 | 2.2 | 2.0 |

*Values are overall means in ng/ml. FSH assay performed using the NIAMDD ovine FSH assay kit (National Pituitary Agency, Bethesda, Maryland, U.S.A.).

Thus, on average, FSH values in the blood of the immunized animals were 12.8% higher than in the control ewes. This small but consistent difference in FSH, especially before cloprostenol injection (see McNatty et al., supra), is sufficient to account for the ovulation-rate differences between the immunized and control groups.

In summary, these findings for the androstenedione-SMP vaccine are at variance with those for the above prior art vaccine, suggesting that the mechanisms of action for the two procedures are different.

Evidence to support the notion that the oil-based androstenedione-SMP vaccine formulation increases both ovulation rates and lambing rates is shown in Table 2.

TABLE 2

Ovulation and lambing-rates using the 6-hydroxyandrost-4-ene-3,17 dione 6-hemisuccinyl Alacen conjugate with an oil-based emulsion in 2.5 year old Romney ewes

| | Ovulation Number | | | | | |
|---|---|---|---|---|---|---|
| | 0 | 1 | 2 | 3 | 4 | 5 |
| Controls (N = 71) | 3 | 49 | 20 | — | — | — |
| Immunised (N = 72) | 1 | 22 | 34 | 13 | 1 | 1 |

| | Lambing Rate | | | | |
|---|---|---|---|---|---|
| | 0 | 1 | 2 | 3 | 4 |
| Controls | 0 | 56 | 11 | — | — |
| Immunised | 6 | 28 | 33 | 5 | — |

Evidence that the water-based (DEAA-dextran) vaccine increases the ovulation rate in ewes is also shown in Table 3.

TABLE 3

Ovulation-rates using 6-hydroxyandrost-4-ene-3,17-dione 6-hemisuccinyl Alacen conjugate with DEAA-dextran adjuvant in 2.5 year old Romney ewes

| | Ovulation number | | | | |
|---|---|---|---|---|---|
| | 0 | 1 | 2 | 3 | Mean |
| Controls (18) | — | 15 | 3 | — | 1.2 ± 0.1 |
| Immunised (18) | — | 9 | 7 | 2 | 1.6 ± 0.2 |

Evidence that a single repeat immunisation of the vaccine leads to a significant ovulation rate reponse in the second year is shown in Table 4.

TABLE 4

Effect of repeat immunisation or no repeat immunisation with androstenedione-Alacenconjugate in an oil-based adjuvant in Coopworth ewes

| Treatment 1984 | Treatment 1985 | Ovulation rate (OR) | | | | | | Overall mean ± standard error of the mean for ovulation rate |
|---|---|---|---|---|---|---|---|---|
| | | 1 | 2 | 3 | 4 | 5 | 6 | |
| Control | — | 32 | 64 | 4 | — | — | — | 1.72 ± 0.05[a] |
| Immunised | Immunised | 8 | 51 | 24 | 13 | 3 | 1 | 2.56 ± 0.10[b] |
| Immunised | — | 26 | 62 | 9 | 3 | — | — | 1.89 ± 0.09[c] | avc = $p < 0.05$; bva, bvc = $p < 0.01$.

When enhancing lambing rates with the androstenedionealacen vaccine the level of antibody titre is invariably below 1:5000. It is known from the prior art that ewes with antibody titres above 1:5000 are unlikely to display overt oestrus behaviour until the titre has fallen below this limit. The significance of antibody titres between 0 and 1:5000 on ovulation rates are unknown. Moreover antibody titre over the mating period has not been shown to correlate with the number of lambs born (see Table 5).

TABLE 5

Antibody titre (reciprocal of geometric mean) and the the number of ewes with 0, 1, 2 or 3 lambs

| Antibody titre at mating (1 geometric mean) | Number of lambs born | Number of ewes |
|---|---|---|
| 464 | 0 | 9 |
| 161 | 1 | 93 |
| 187 | 2 | 57 |
| 1002 | 3 | 1 |

Animals were 2.5 year old Romney ewes immunised with androstenedione conjugated to bovine serum albumin in Freund's complete adjuvant With regard to vaccination procedures all that is known with certainty is that high antibody titres (i.e., >1:5000) are not desirable. This antibody titre limit is rarely, if ever, exceeded over the mating period when androstenedione-SMP conjugate is formulated for vaccination into ewes by the above methods and when mating is not permitted to occure for the first four weeks after the second injection in the first year and the time of the administration of the booster injection in subsequent years.

The above androstenedione-SMP conjugate vaccine may be prepared for injection into ewes by two different procedures. The first procedure involves mixing the androstenedione-SMP conjugate with Sontex 55 USP (a light mineral oil) and an oil-water emulsifier [Tween 85 (Polysorbate 85):Span 85 (Sorbitan trioleate), 50/50 v/v]. To prepare the vaccine with these materials, the freeze-dried conjugate preparation is dissolved in sterile saline (NaCl 0.85/liter; 100 ml) and 50–100 ml of Sontex is then emulsified with 25 ml of Tween 85/Span 85 and the conjugate solution. This mixture will remain in a stable emulsified form for at least 48 h at 4° C. In freeze-dried form the vaccine retains its biological potency. The quantity of the conjugate dissolved in saline is calculated so that the amount administered to each ewe is 3 to 5 mg. Normally, the volume of vaccine administered to each ewe is limited to 1 ml.

The second procedure requires dissolving the conjugate in an aqueous solution of diaminoethyl dextran (M.W.≈500,000; 5% w/v). In contrast to the emulsified form of the vaccine (i.e., the 1st procedure), the volume of material need not be limited to 1 ml, however, it is important that the total amount of the conjugate administered to each ewe is between 3 and 5 mg.

The advantages of the oil based vaccine formulation are as follows: 1. The antibody titre response to the double injection regime outlined above is prolonged and highly reproducible. For example, the reciprocal geometric mean antibody titres will normally remain between 100 and 2000 for over 200 days. This shows that the time onset of mating need not begin 5 weeks after the second injection but could be delayed for several weeks if necessary. 2. There is a significant "carry-over" effect of the vaccine with respect to ovulation rates during the second breeding season. That is, even if a repeat immunisation is not performed during the breeding season following that in which the primary immunisation procedure is performed, the ovulation rate in the immunised ewes is significantly higher than that in the controls (Table 4).

The disadvantages of the oil-based vaccine are as follows: 1. The vaccine needs to be used within 48 hours of mixing and preferably within 24 hours of injection. However, the emulsification procedure does not require sophisticated equipment. For example, it could be done with an electric food mixer. 2. If excess oil is administered under the skin or, if the oil is inadvertently injected into muscle, the potential for unsightly lumps or lesions are created. This can be eliminated or reduced by ensuring the injection volume is kept to 1 ml or less. In other words, provided the total amount of oil to be injected is kept below half ml no problems should arise. However, even if lumps do form there is no long-term carcass damage as the lumps or injection sites are not visible even at the level of the microscope some 12 months after the last injection.

We claim:

1. A fertility vaccine comprising an effective amount of an immunogenic conjugate of 6-hydroxyandrost-4-ene-3,17-dione linked through the 6-hydroxyl group to a soluble milk protein (SMP), in admixture with a suitable adjuvant.

2. A fertility vaccine according to claim 1 wherein the SMP is a whey protein concentrate having a protein content of at least 50% by weight.

3. A fertility vaccine according to claim 1 wherein the soluble milk protein is a whey protein concentrate derived from the ultrafiltration of rennet casein whey.

4. A fertility vaccine according to claim 1 wherein the SMP is a whey protein concentrate of the ALACEN range (as hereinbefore defined).

5. A method of preparing an immunogenic conjugate of 6-hydroxyandrost-4-ene-3,17-dione 6-hemisuccinate soluble-milk protein (SMP) comprising the steps of:
   (1) reaction of androst-4-ene-3,17-dione with acetic anhydride to produce 3-acetoxyandrost-3,5-diene-17-one,
   (2) addition of meta-chloroperbenzoic acid to the product of step (1) and reaction to form a mixture of 6α- and 4β-hydroxyandrost-4-ene-3,17-dione,
   (3) reacting the product of step (2) with succinic anhydride to produce 6-hydroxyandrost-4-ene-3,17-dione hemisuccinate,
   (4) reacting the product of step (3) with SMP so that the free acid group of the β-hydroxyandrost-4-ene-3,17-dione hemisuccianate is linked to the free amino residues on the protein to form the conjugate 6-hydroxyandrost-4-ene-3,17-dione 6-hemisuccinyl SMP.

6. A method according to claim 5 wherein the reaction of step (2) takes place in the presence of dioxan and water.

7. A method according to claim 5 wherein the reaction mixture of step (3) is kept at substantially 5° C. for 24 hours and the organic phase subsequently washed and dried.

8. A method according to claim 5 wherein step (4) takes place by mixing the product of step (3) with N-hydroxysuccinamide, dicyclohexyl carbonimide and tetrahydrofuran.

9. A fertility vaccine according to claim 1 comprising an effective amount of 6-hydroxyandrost-4-ene-3,17-dione 6-hemisuccinyl soluble milk protein concentrate.

10. A fertility vaccine according to claim 1 wherein the conjugate is dissolved in an aqueous solution of diaminoethyl dextran.

11. A fertility vaccine according to claim 10 wherein the diaminoethyl dextran is at a concentration of substantially 5% w/v.

12. A method of increasing the fertility of a flock of sheep comprising the administration of a fertility increasing amount of vaccine according to claim 1 to the ewes of the flock.

13. A method according to claim 12 wherein the ewes of a flock are injected with the vaccine twice in the first year of treatment and once each year for subsequent years.

14. A method according to claim 13 wherein the first year injections are administered at least 8 weeks before the commencement of mating and then between 5 to 4 weeks before the commencement of mating.

15. A method according to claim 14 wherein each injection administers between 3 and 5 mg of the conjugate 6-hydroxyandrost-4-ene-3,17-dione 6-hemisuccinyl SMP.

16. A method according to claim 6 wherein the reaction mixture of step (3) is kept at substantially 5° C. for 24 hours and the organic phase subsequently washed and dried.

* * * * *